(12) United States Patent
Je et al.

(10) Patent No.: US 8,071,226 B2
(45) Date of Patent: Dec. 6, 2011

(54) RED PHOSPHORESCENT COMPOUNDS AND ORGANIC ELECTROLUMINESCENT DEVICES USING THE SAME

(75) Inventors: Jong-Tae Je, Chungcheongbuk-do (KR); Sug-Kwang Hwang, Chungcheongbuk-do (KR); Seon-Keun Yoo, Chungcheongbuk-do (KR); Hyun-Jung Kwon, Chungcheongbuk-do (KR); Nam-Yi Kim, Chungcheongbuk-do (KR)

(73) Assignee: SFC Co. Ltd (KR)

( * ) Notice: Subject to any disclaimer, the term of this patent is extended or adjusted under 35 U.S.C. 154(b) by 915 days.

(21) Appl. No.: 12/034,732

(22) Filed: Feb. 21, 2008

(65) Prior Publication Data

US 2009/0104472 A1    Apr. 23, 2009

(30) Foreign Application Priority Data

Oct. 18, 2007    (KR) .................. 10-2007-0105131

(51) Int. Cl.
*H01L 51/54* (2006.01)
*C09K 11/06* (2006.01)

(52) U.S. Cl. . 428/690; 428/917; 313/504; 257/E51.044; 546/10

(58) Field of Classification Search ............... None
See application file for complete search history.

(56) References Cited

U.S. PATENT DOCUMENTS

2001/0019782 A1 * 9/2001 Igarashi et al. ............... 428/690
2003/0072964 A1 * 4/2003 Kwong et al. ................. 428/690
2007/0278936 A1 * 12/2007 Herron et al. ................. 313/504

FOREIGN PATENT DOCUMENTS

KR    10-2005-0081032    8/2005

* cited by examiner

*Primary Examiner* — Marie R. Yamnitzky
(74) *Attorney, Agent, or Firm* — Alston & Bird LLP (57) ABSTRACT

Provided are red phosphorescent compounds represented by Formula 1:

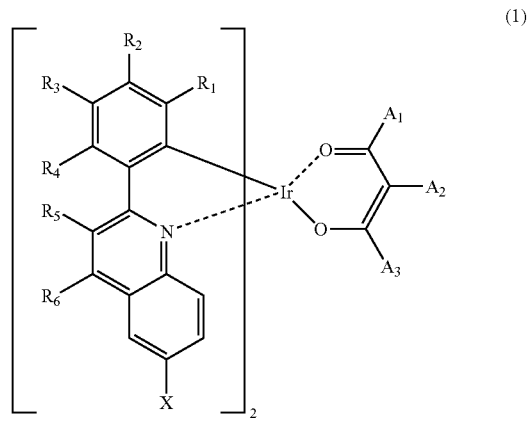

(1)

Organic electroluminescent devices using the red phosphorescent compounds are further provided. The organic electroluminescent devices exhibit good red color purity, high quantum efficiency, high power efficiency, high luminance, and long lifetime.

8 Claims, 1 Drawing Sheet

FIG. 1

RED PHOSPHORESCENT COMPOUNDS AND ORGANIC ELECTROLUMINESCENT DEVICES USING THE SAME

CROSS-REFERENCE TO RELATED APPLICATIONS

The present application claims priority to Korean Patent Application No. 10-2007-0105131, filed Oct. 18, 2007, the entire contents of which are incorporated herein by reference.

FIELD OF THE INVENTION

The present invention relates to red phosphorescent compounds and organic electroluminescent devices using the same. More specifically, the present invention relates to red phosphorescent compounds that can be used to fabricate organic electroluminescent devices with good red color purity, high quantum efficiency, high luminance, high power efficiency and long lifetime, and organic electroluminescent devices using the red phosphorescent compounds.

BACKGROUND

As displays have become larger in size in recent years, there has been an increasing demand for flat panel display devices that take up little space. Liquid crystal display devices as representative flat panel display devices can be reduced in weight when compared to the prior art cathode ray tubes (CRTs), but have several disadvantages in that the viewing angle is limited, the use of backlight is inevitably required, etc. Organic light-emitting diodes (OLEDs) as a new type of flat panel display devices are self-emissive display devices. Organic light-emitting diodes have the advantages of a large viewing angle, light weight, small thickness, small size and rapid response time over liquid crystal display devices.

Organic electroluminescent devices are characterized by their low driving voltage (e.g., 10V or below), broad viewing angle, rapid response time, high contrast, etc., in comparison with plasma display panels (PDPs) and inorganic electroluminescent display devices. These characteristics allow the use of organic electroluminescent devices as pixels of graphic displays, television image displays and surface light sources. In addition, organic electroluminescent devices can be fabricated on flexible transparent substrates, can be reduced in thickness and weight, and have good color representation. Therefore, organic electroluminescent devices are recognized as promising devices for use in next-generation flat panel displays (FPDs).

Typical organic electroluminescent devices comprise a first electrode as a hole injection electrode (anode), a second electrode as an electron injection electrode (cathode), and an organic light-emitting layer disposed between the anode and the cathode wherein holes injected from the anode and electrons injected from the cathode combine with each other in the organic light-emitting layer to form electron-hole pairs (excitons), and then the excitons fall from the excited state to the ground state and decay to emit light. The applicability of organic electroluminescent devices to full-color displays is expected. To obtain full colors, it is necessary to arrange pixels emitting light of three primary colors of green, red and blue on a panel. Various methods have been suggested to arrange pixels on a panel. Such methods include: i) the arrangement of three types of organic electroluminescent devices emitting blue, green and red light, ii) the separation of light emitted from a white (a mixed color of the primary colors (RGB)) light-emitting device into three primary colors through a color filter, and iii) the use of light emitted from a blue organic light-emitting device as a source of fluorescence emission to convert the light to green and red light. In any case, red light emission is essentially required. Thus, red light emission has been the subject of intense research.

Organic electroluminescent devices consist essentially of a transparent electrode as an anode, an organic light-emitting layer including a light-emitting region and a metal electrode as a cathode. The type of the organic electroluminescent devices (i.e. blue, green and red light-emitting devices) will be determined depending on what kind of material is used for the formation of the light-emitting layer.

The principle of light emission from a light-emitting material is as follows. Electrons and holes injected from respective electrodes combine with each other to form excitons. At this time, singlet excitons and triplet excitons are involved in fluorescence and phosphorescence processes, respectively. Phosphorescent materials using triplet excitons whose probability of formation is 75% exhibit higher luminescence efficiency than fluorescent materials using singlet excitons whose probability of formation is 25%. Molecules that readily undergo phosphorescence emission are metal complexes containing high atomic number metals in which intersystem crossing occurs readily. Particularly, iridium complex compounds have received considerable attention due to their high phosphorescence efficiency.

Korean Unexamined Patent Publication No. 10-2005-81032 suggests a red phosphorescent material using an iridium metal complex represented by the following formula:

wherein M is Ir, Rh, Re or Os; $R^1$, $R^2$, $R^3$, $R^4$, $R^5$ and $R^6$ are independently hydrogen, $C_1$-$C_{20}$ alkyl, $C_1$-$C_{20}$ aryl, $C_1$-$C_{20}$ cycloalkyl, halogen, a linear or branched substituent with at least one halogen atom, a linear or branched substituent with at least one hetero atom, carbonyl, carboxyl, vinyl, acetylenyl or trialkylsilyl, the adjacent groups may be bonded together to form a ring; and L is an ancillary ligand.

As the red color purity of an organic electroluminescent device using the red phosphorescent material increases (i.e. the x values on CIE chromaticity coordinates increase), the lifetime of the organic electroluminescent device is shortened and the luminance, quantum yield and power efficiency of the device decrease.

SUMMARY OF THE INVENTION

Therefore, it is a first object of the present invention to provide red phosphorescent compounds that can be used to fabricate organic electroluminescent devices with good red color purity, high luminescence efficiency, and long lifetime.

It is a second object of the present invention to provide organic electroluminescent devices using the red phosphorescent compounds.

In accordance with the present invention, the first object is achieved by the provision of a red phosphorescent compound of Formula 1:

(1)

wherein $R_1$, $R_2$, $R_3$, $R_4$, $R_5$ and $R_6$ are independently a hydrogen atom, a $C_1$-$C_{18}$ alkyl group, a $C_1$-$C_{18}$ alkoxy group, a halogen atom, a $C_1$-$C_{18}$ haloalkyl group, a substituted or unsubstituted $C_5$-$C_{18}$ aryl group, a $C_5$-$C_{18}$ cycloalkyl group, or a 5- to 18-membered aromatic heterocyclic group containing at least one heteroatom selected from N, O and S atoms, with the proviso that the substituted aryl group and the heteroaryl group is substituted with at least one substituent selected from the group consisting of $C_1$-$C_{10}$ alkyl, $C_1$-$C_{10}$ alkoxy, cyano, $C_1$-$C_{10}$ alkylamino, $C_1$-$C_{10}$ alkylsilyl, halogen, $C_6$-$C_{10}$ aryl, $C_6$-$C_{10}$ aryloxy, $C_6$-$C_{10}$ arylamino, $C_6$-$C_{10}$ arylsilyl, $C_3$-$C_{19}$ heteroaryl and hydrogen; each X is a trialkylsilyl group; and $A_1$, $A_2$ and $A_3$ are independently a hydrogen atom, a $C_1$-$C_{18}$ alkyl group, a halogen atom, a $C_1$-$C_{18}$ haloalkyl group, a $C_5$-$C_{18}$ aryl group or a $C_5$-$C_{18}$ cycloalkyl group, with the proviso that $A_2$ is optionally bonded to $A_1$ or $A_3$ to form a ring.

In an embodiment of the present invention, each X in Formula 1 is a trimethylsilyl (TMS) group.

In a further embodiment of the present invention, the red phosphorescent compound may be selected from the group consisting of the following compounds (2-1 to 2-20):

(2-1)

-continued (2-2)

(2-3)

(2-4)

(2-5)

(2-6)

(2-7)

(2-8)

(2-9)

(2-10)

(2-11)

(2-12)

(2-13)

(2-14)

(2-18)

(2-15)

(2-19)

and (2-16)

(2-20)

(2-17)

In accordance with the present invention, the second object is achieved by the provision of an organic electroluminescent device comprising an anode, an organic light-emitting layer and a cathode wherein the organic light-emitting layer contains the compound of Formula 1 or one of the compounds 2-1 to 2-20.

In an embodiment of the present invention, the organic electroluminescent device may further comprise a hole transport layer, a hole injecting layer, an electron transport layer and an electron injecting layer.

BRIEF DESCRIPTION OF THE DRAWING

The above and other objects, features and other advantages of the present invention will be more clearly understood from the following detailed description taken in conjunction with the accompanying drawing, in which.

DETAILED DESCRIPTION OF THE PREFERRED EMBODIMENTS

Exemplary embodiments of the present invention will now be described in more detail. However, these embodiments do not serve to limit the invention.

As depicted in Formula 1, the red phosphorescent compound of the present invention has trialkylsilyl groups substituted at the 6-positions of the quinoline rings. Due to the presence of the substituents, the red phosphorescent compound can be used to fabricate an organic electroluminescent device with good red color purity, high quantum efficiency, high luminance, high power efficiency and long lifetime.

The trialkylsilyl groups may be trimethylsilyl as illustrated in Formula 2-1 to 2-20, but are not limited thereto.

The organic electroluminescent device of the present invention uses an organic light-emitting layer containing the red phosphorescent compound.

Specifically, the organic electroluminescent device of the present invention comprises an anode for generating holes, a cathode for generating electrons and a light-emitting layer disposed between the anode and the cathode to receive the holes and the electrons emitted from the anode and the cathode, respectively, wherein the light-emitting layer contains the red phosphorescent compound.

Due to the presence of the light-emitting layer containing the red phosphorescent compound, the organic electroluminescent device can exhibit the same excellent characteristics as the red phosphorescent compound.

A more detailed explanation of the organic electroluminescent device according to the present invention will be provided below with reference to the accompanying drawing.

Figure 1:
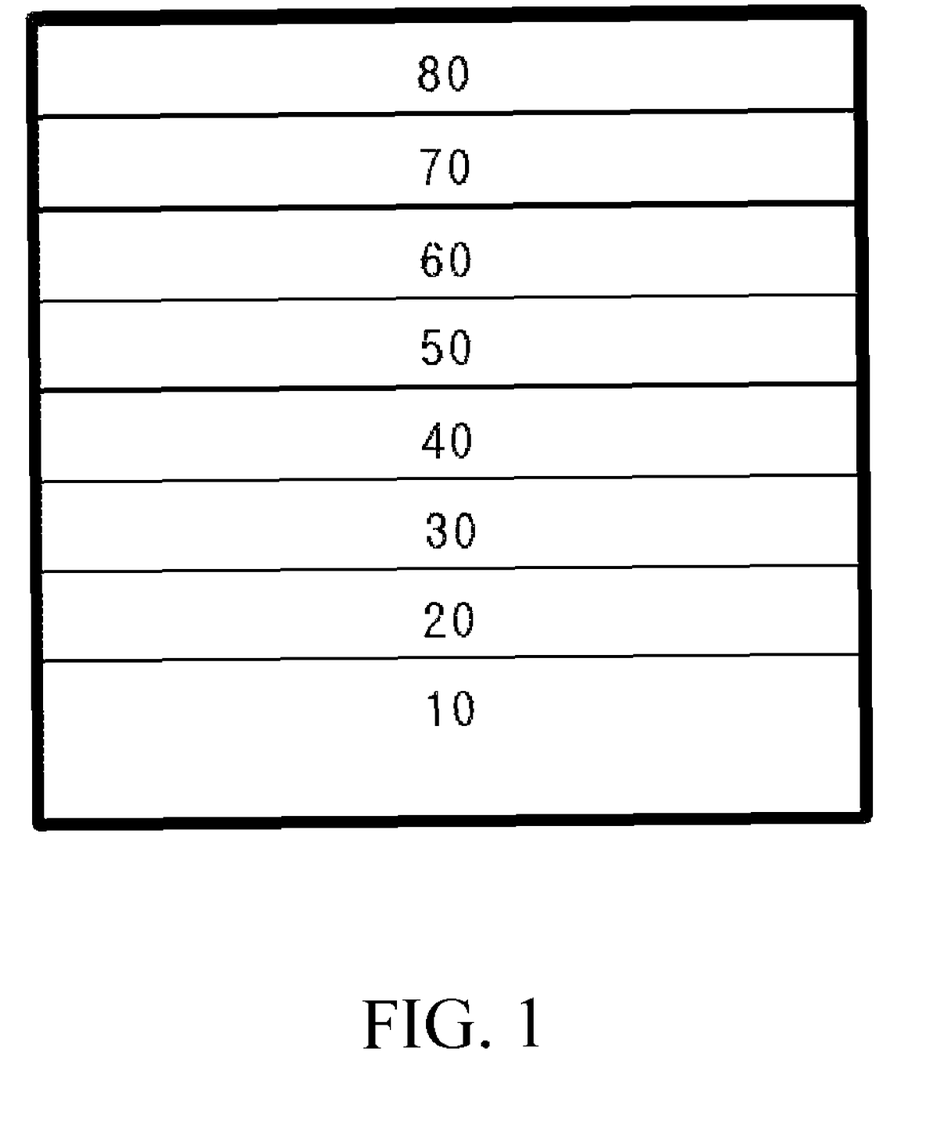
FIG. 1 is a schematic cross-sectional view of an organic electroluminescent device according to an embodiment of the present invention.

FIG. 1 is a cross-sectional view illustrating the structure of an organic electroluminescent device according to an embodiment of the present invention. Referring to FIG. 1, the organic electroluminescent device of the present invention comprises a substrate 10, an anode 20, a hole transport layer 40, an organic light-emitting layer 50, an electron transport layer 60, and a cathode 80. If needed, the organic electroluminescent device may further comprise a hole injecting layer 30 and an electron injecting layer 70. The organic electroluminescent device may further comprise one or two intermediate layers, a hole blocking layer or an electron blocking layer, all of which are not shown in FIG. 1.

With reference to FIG. 1, the organic electroluminescent device of the present invention and a fabrication method thereof will be explained below. First, an anode material is coated on a substrate 10 to form an anode 20. The substrate 10 may be one used in common organic electroluminescent (EL) devices. An organic or transparent plastic substrate is preferred in terms of transparency, surface smoothness, ease of handling and waterproofness. As the anode material, there may be used a highly transparent and electrically conductive material, for example, indium tin oxide (ITO), indium zinc oxide (IZO), tin oxide ($SnO_2$) or zinc oxide (ZnO). Optionally, a hole injecting material is applied to the anode 20 by thermal evaporation under vacuum or spin coating to form a hole injecting layer 30. The hole injecting layer 30 induces a smooth flow of holes to improve the functions of the device. Any material that is commonly used in the art may be used without any particular limitation to form the hole injecting layer. Suitable materials for the hole injecting layer include the following compounds:

(CuPc)

HIL-1

(TCTA)

HIL-2

(m-MTDATA)

HIL-3

-continued

HIL-4

(DAPEB)

In the above formulas, TCTA, m-MTDATA and DAPEB are starburst amines.

A hole transport material is applied to the hole injecting layer 30 by thermal evaporation under vacuum or spin coating to form a hole transport layer 40. The hole transport layer serves to facilitate the injection of holes from the anode. An electron-donating compound having a low ionization potential is used to form the hole transport layer. Examples of widely used electron-donating compounds include diamine, triamine and tetraamine derivatives whose basic skeleton is triphenylamine. Any material that is commonly used in the art may be used to form the hole transport layer, and examples thereof include, but are not limited to, the following compounds:

HTL-1

(TPD)

HTL-2

(α-NPD)

In the above formulas, TPD and α-NPD represent N,N'-bis(3-methylphenyl)-N,N'-diphenyl-[1,1'-biphenyl]-4,4'-diamine and N,N'-di(naphthalen-1-yl)-N,N'-diphenylbenzidine, respectively.

Subsequently, an organic light-emitting layer 50 is formed on the hole transport layer 40. The red phosphorescent compound may be used singly or as a dopant material to form the organic light-emitting layer 50. In the latter case, the organic light-emitting layer is of a host/dopant system. When the red phosphorescent compound is used as a single material for the organic light-emitting layer, a broad peak is observed in the long-wavelength region, resulting in poor color purity, and luminescence quenching occurs, resulting in poor efficiency. It is, therefore, preferable to use the red phosphorescent compound as a dopant material for the formation of the organic light-emitting layer of a host/dopant system. Any host material well known in the art may be used without any particular limitation in the present invention. Examples of suitable host materials include aluminum complexes, such as (1,1'-bisphenyl-4-olato)bis(2-methyl-8-quinolinolate-N1,O8)aluminum (II) (BAlq) and tris(8-quinolinolato)aluminum (Alq$_3$), zinc complexes, coumarin derivatives, and carbazole derivatives. In the aluminum and zinc complexes, suitable ligands are quinoline, biphenyl, isoquinol, phenyl, methylquinol, dimethylquinol and dimethylisoquinol groups. A preferred carbazole derivative is 4,4'-N,N'-dicarbazole-biphenyl(CBP).

A hole blocking layer (not shown) is optionally formed on the organic light-emitting layer 50. The hole blocking layer is formed of a material whose HOMO level is very low to eliminate the problems, i.e. short lifetime and low efficiency of the device, which are encountered when holes enter the cathode through the organic light-emitting layer. The hole blocking material is not particularly restricted, but it must have the ability to transport electrons and a higher ionization potential than the light-emitting compound.

Representative hole blocking materials are BAlq, 2,9-dimethyl-4,7-diphenyl-1,10-phenanthroline (BCP), 1,3,5-tris(N-phenylbenzimidazol-2-yl)benzene (TPBI), etc. The organic electroluminescent device may further comprise an electron transport layer 60 formed on the hole blocking layer. The electron transport layer serves to sufficiently transport electrons from the cathode to the organic light-emitting layer, and to inhibit the migration of unbound holes in the organic light-emitting layer, thereby increasing the opportunity for the unbound holes to recombine with the electrons in the light-emitting layer. It is to be understood that any material can be used without any particular limitation to form the electron transport layer so long as it is commonly used in the art. Examples of suitable electron transport materials include anthracene derivatives, pyrene derivatives and oxadiazole derivatives, such as PBD, BMD, BND and Alq$_3$. Some of the electron transport materials are the following compounds:

ETL-1

ETL-2

ETL-3

ETL-4

ETL-5

(PBD)

ETL-6

(BMD)

ETL-7

(BND)

The organic electroluminescent device of the present invention may further optionally comprise an electron injecting layer 70 disposed on the electron transport layer. The electron injecting layer facilitates the injection of electrons from the cathode, thus contributing to an improvement in the power efficiency of the device. The electron injecting layer may be formed using any suitable material known in the art. Examples of such electron injecting materials include, but are not particularly limited to, LiF, NaCl, CsF, $Li_2O$ and BaO.

A cathode metal is deposited on the electron injecting layer 70 by thermal evaporation under vacuum to form a cathode 80, completing the fabrication of the organic EL device. As the cathode metal, there may be used, for example, lithium (Li), magnesium (Mg), aluminum (Al), aluminum-lithium (Al—Li), calcium (Ca), magnesium-indium (Mg—In) or magnesium-silver (Mg—Ag). A light-transmissive cathode made of ITO or IZO may be used to fabricate a top emission type device.

Hereinafter, the present invention will be explained in more detail with reference to the following examples. However, these examples are not intended to limit the present invention.

EXAMPLES

Example 1

Example 1-(1)

Synthesis of iridium (III) (2-(3,5-dimethylphenyl)-6-trimethylsilylquinolinato-N,$C^{2'}$)$_2$(2,4-pentanedionate-O,O)

15.0 g (0.05 mole) of 2-(3,4-dimethylphenyl)-6-trimethylsilylquinoline, 7.0 g (0.02 mole) of iridium (III) chloride hydrate (Ir(III)Cl$_3$·3H$_2$O), 140 ml of 2-ethoxyethanol and 70 ml of distilled water (H$_2$O) were refluxed in a dry three-neck round-bottom flask for 24 hours and cooled to room temperature. Water was added to the reaction mixture to precipitate a crystal. The crystal was collected by filtration and washed with water to give 10.0 g of a dimeric complex. 10.0 g (0.01 mole) of the dimeric complex, 1.3 g (0.01 mole) of acetylacetone, 2.5 g (0.02 mole) of sodium carbonate ($Na_2CO_3$) and 200 ml of 2-ethoxyethanol were stirred in a dry three-neck round-bottom flask at room temperature for 24 hours. Then water was added to the reaction mixture to precipitate a crystal. The crystal was collected by filtration and washed with methanol, affording 3.8 g of the title compound.

$^1$H NMR (300 MHz, $CDCl_3$): δ 8.02-8.12 (d, 4H), 7.79-7.89 (dd, 4H), 7.58-7.66 (s, 2H), 7.41-7.49 (dd, 2H), 6.46-6.58 (s, 2H), 4.20-4.38 (s, 1H), 2.30-2.42 (s, 6H), 1.30-1.38 (s, 6H), 1.22-1.30 (s, 6H), 0.25-0.35 (s, 18H)

Example 1-(2)

Fabrication of Organic Electroluminescent Device

ITO glass as an anode was patterned to have a light-emitting area of 3 mm×3 mm, followed by cleaning. After the anode was mounted in a vacuum chamber, the pressure of the chamber was adjusted to $1 \times 10^{-6}$ torr. A hole injecting layer (700 Å) composed of HIL-1 (CuPc) (see, the compounds of Formulae 3) and a hole transport layer (300 Å) composed of HTL-2 (α-NPD) (see, the compounds of Formulae 4) were sequentially formed on the anode. Thereafter, a mixture of BAlq and the iridium complex compound (7%) prepared in Example 1-(1) was coated on the hole transport layer to form a 250 Å thick organic light-emitting layer. Then, an electron transport layer (350 Å) composed of ETL-4 (see, the compounds of Formulae 5), an electron injecting layer (5 Å) composed of LiF and an Al cathode (700 Å) were formed in this order on the organic light-emitting layer to fabricate an organic electroluminescent device.

Example 2

Example 2-(1)

Synthesis of iridium (III) (2-(3,5-dimethylphenyl)-6-trimethylsilylquinolinato-N,$C^{2'}$)$_2$(3-methyl-2,4-pentanedionate-O,O)

27.5 g (0.09 mole) of 2-(3,5-dimethylphenyl)-6-trimethylsilylquinoline, 12.8 g (0.04 mole) of iridium (III) chloride hydrate (Ir(III)$Cl_3$·$3H_2O$), 384 ml of 2-ethoxyethanol and 128 ml of distilled water ($H_2O$) were refluxed in a dry three-neck round-bottom flask for 24 hours and cooled to room temperature. Water was added to the reaction mixture to precipitate a crystal. The crystal was collected by filtration and washed with water to give 30.0 g of a dimeric complex. 15.0 g (0.01 mole) of the dimeric complex, 3.1 g (0.03 mole) of 3-methyl-2,4-pentanedione, 3.8 g (0.04 mole) of sodium carbonate ($Na_2CO_3$) and 300 ml of 2-ethoxyethanol were stirred in a dry three-neck round-bottom flask at room temperature for 24 hours. After completion of the reaction, water was added to the reaction mixture to precipitate a crystal. The crystal was collected by filtration and washed with methanol, affording 8.2 g of the title compound.

$^1$H NMR (300 MHz, $CDCl_3$): δ 8.02-8.10 (s, 4H), 7.85-7.91 (d, 2H), 7.79-7.85 (d, 2H), 7.61-7.67 (s, 2H), 7.40-7.49 (dd, 2H), 6.50-6.61 (s, 2H), 2.36-2.44 (s, 6H), 1.39-1.48 (s, 6H), 1.24-1.34 (s, 6H), 0.96-1.04 (s, 3H), 0.28-0.34 (s, 18H)

Example 2-(2)

Fabrication of Organic Electroluminescent Device

An organic electroluminescent device was fabricated in the same manner as in Example 1 except that the iridium complex compound prepared in Example 2-(1) was used instead of the iridium complex compound prepared in Example 1-(1).

Example 3

Example 3-(1)

Synthesis of iridium (III) (2-(2,4-dimethylphenyl)-6-trimethylsilylquinolinato-N,$C^{2'}$)$_2$(2,2,6,6-tetramethyl-3,5-heptanedionate-O,O)

9.0 g (0.03 mole) of 2-(2,4-dimethylphenyl)-6-trimethylsilylquinoline, 4.5 g (0.01 mole) of iridium (III) chloride hydrate (Ir(III)$Cl_3$·$3H_2O$), 150 ml of 2-ethoxyethanol and 50 ml of distilled water ($H_2O$) were refluxed in a dry three-neck round-bottom flask for 24 hours. After the reaction was finished, the reaction mixture was cooled to room temperature and water was added thereto to precipitate a crystal. The crystal was collected by filtration and washed with water to give 10.4 g of a dimeric complex. 10.0 g (0.01 mole) of the dimeric complex, 2.2 g (0.01 mole) of 2,2,6,6-tetramethyl-3,5-heptanedione, 2.5 g (0.02 mole) of sodium carbonate ($Na_2CO_3$) and 200 ml of 2-ethoxyethanol were stirred in a dry three-neck round-bottom flask at room temperature for 24 hours. Then, water was added to the reaction mixture to precipitate a crystal. The crystal was collected by filtration and washed with methanol, affording 5.8 g of the title compound.

$^1$H NMR (300 MHz, $CDCl_3$): δ 8.20-8.35 (d, 2H), 8.00-8.18 (dd, 4H), 7.75-7.88 (s, 2H), 7.31-7.45 (d, 2H), 6.52-6.65 (s, 2H), 6.32-6.45 (s, 2H), 4.60-4.75 (s, 1H), 2.80-2.98 (s, 6H), 1.85-2.03 (s, 6H), 0.48-0.72 (s, 18H), 0.20-0.38 (s, 18H)

Example 3-(2)

Fabrication of Organic Electroluminescent Device

An organic electroluminescent device was fabricated in the same manner as in Example 1 except that the iridium complex compound prepared in Example 3-(1) was used instead of the iridium complex compound prepared in Example 1-(1).

Example 4

Example 4-(1)

Synthesis of iridium (III) (2-(4-methylphenyl)-3-methyl-6-trimethylsilylquinolinato-N,$C^{2'}$)$_2$(2,2,6,6-tetramethyl-3,5-heptanedionate-O,O)

12.8 g (0.05 mole) of 2-(4-methylphenyl)-3-methyl-6-trimethylsilylquinoline, 7.5 g (0.02 mole) of iridium (III) chloride hydrate (Ir(III)$Cl_3$·$3H_2O$), 150 ml of 2-ethoxyethanol and 75 ml of distilled water ($H_2O$) were refluxed in a dry three-neck round-bottom flask for 24 hours. After the reaction was finished, the reaction mixture was cooled to room temperature and water was added thereto to precipitate a crystal. The crystal was collected by filtration and washed with water to give 10.0 g of a dimeric complex.

10.0 g (0.01 mole) of the dimeric complex, 2.2 g (0.01 mole) of (2,2,6,6-tetramethyl-3,5-heptanedione), 2.5 g (0.02 mole) of sodium carbonate ($Na_2CO_3$) and 200 ml of 2-ethoxyethanol were stirred in a dry three-neck round-bottom flask at room temperature for 24 hours. Water was added to the reaction mixture to precipitate a crystal. The crystal was collected by filtration and washed with methanol, affording 1.1 g of the title compound.

$^1$H NMR (300 MHz, $CDCl_3$): δ 7.98-8.08 (dd, 4H), 7.85-7.94 (s, 2H), 7.72-7.80 (s, 2H), 7.28-7.36 (d, 2H), 6.78-6.85 (d, 2H), 6.56-6.65 (s, 2H), 4.50-4.65 (s, 1H), 2.98-3.18 (s, 6H), 1.95-2.12 (s, 6H), 0.48-0.70 (s, 18H), 0.20-0.45 (s, 18H)

Example 4-(2)

Fabrication of Organic Electroluminescent Device

An organic electroluminescent device was fabricated in the same manner as in Example 1 except that the iridium complex compound prepared in Example 4-(1) was used instead of the iridium complex compound prepared in Example 1-(1).

Example 5

Example 5-(1)

Synthesis of iridium (III) (2-(3,5-dimethylphenyl)-6-trimethylsilylquinolinato-N,$C^{2'}$)$_2$(2,2,6,6-tetramethyl-3,5-heptanedionate-O,O)

27.5 g (0.09 mole) of 2-(3,5-dimethylphenyl)-6-trimethylsilylquinoline, 12.8 g (0.04 mole) of iridium (III) chloride hydrate (Ir(III)$Cl_3$.3$H_2O$), 384 ml of 2-ethoxyethanol and 128 ml of distilled water ($H_2O$) were refluxed in a dry three-neck round-bottom flask for 24 hours. After completion of the reaction, the reaction mixture was cooled to room temperature and water was added thereto to precipitate a crystal. The crystal was collected by filtration and washed with water to give 30.0 g of a dimeric complex. 15.0 g (0.01 mole) of the dimeric complex, 5.0 g (0.03 mole) of 2,2,6,6-tetramethyl-3,5-heptanedione, 3.8 g (0.04 mole) of sodium carbonate ($Na_2CO_3$) and 300 ml of 2-ethoxyethanol were stirred in a dry three-neck round-bottom flask at room temperature for 24 hours. Water was added to the reaction mixture to precipitate a crystal. The crystal was collected by filtration and washed with methanol, affording 9.0 g of the title compound.

$^1$H NMR (300 MHz, $CDCl_3$): δ 7.98-8.06 (s, 4H), 7.74-7.80 (dd, 4H), 7.59-7.65 (s, 2H), 7.35-7.44 (dd, 2H), 6.50-6.58 (s, 2H), 4.50-4.65 (s, 1H), 2.36-2.44 (s, 6H), 1.29-1.38 (s, 6H), 0.56-0.64 (s, 18H), 0.25-0.32 (s, 18H)

Example 5-(2)

An organic electroluminescent device was fabricated in the same manner as in Example 1 except that the iridium complex compound prepared in Example 5-(1) was used instead of the iridium complex compound prepared in Example 1-(1).

Comparative Example 1

Comparative Example 1-(1)

Synthesis of Iridium Complex Compound

The above iridium complex compound was prepared to compare with the red phosphorescent compounds of the present invention.

Trimethylsilyl (TMS) groups are substituted at the 4-positions of the phenyl rings and methyl groups are substituted at the 6-positions of the quinoline rings in the comparative compound, whereas trimethylsilyl groups are substituted at the 6-positions of the quinoline rings in the compounds of the present invention.

The comparative iridium complex compound was prepared by the following procedure. First, 16.3 g (0.06 mole) of 2-(4-trimethylsilylphenyl)-6-methylquinoline, 8.0 g (0.03 mole) of iridium (III) chloride hydrate (Ir(III)$Cl_3$.3$H_2O$), 160 ml of 2-ethoxyethanol and 80 ml of distilled water ($H_2O$) were refluxed in a dry three-neck round-bottom flask for 24 hours. After completion of the reaction, the reaction mixture was cooled to room temperature and water was added thereto to precipitate a crystal. The crystal was collected by filtration and washed with water to give 15.0 g of a dimeric complex. 15.0 g (0.01 mole) of the dimeric complex, 2.0 g (0.02 mole) of acetylacetone, 3.9 g (0.04 mole) of sodium carbonate ($Na_2CO_3$) and 300 ml of 2-ethoxyethanol were stirred in a dry three-neck round-bottom flask at room temperature for 24 hours.

Thereafter, water was added to the reaction mixture to precipitate a crystal. The crystal was collected by filtration and washed with methanol, affording 3.0 g of the target product.

$^1$H NMR (300 MHz, $CDCl_3$): δ 8.40-8.50 (d, 2H), 8.00-8.16 (dd, 4H), 7.70-7.80 (d, 2H), 7.55-7.62 (s, 2H), 7.20-7.30 (dd, 2H), 7.05-7.12 (d, 2H), 6.62-6.70 (s, 2H), 4.74-4.80 (s, 1H), 2.45-2.65 (s, 6H), 1.45-1.65 (s, 6H), 0.05-0.30 (s, 18H)

Comparative Example 1-(2)

Fabrication of Organic Electroluminescent Device

An organic electroluminescent device was fabricated in the same manner as in Example 1 except that the iridium complex compound prepared in Comparative Example 1-(1) was used instead of the iridium complex compound prepared in Example 1-(1).

Comparative Example 2

Comparative Example 2-(1)

Synthesis of Iridium Complex Compound

The above iridium complex compound was prepared to compare with the red phosphorescent compounds of the present invention.

In the structure of the comparative compound, trimethylsilyl (TMS) groups are substituted at the 4-positions of the phenyl rings and methyl groups are substituted at the 6- and 10-positions of the quinoline rings.

The comparative iridium complex compound was prepared by the following procedure. First, 30.0 g (0.10 mole) of 2-(4-trimethylsilylphenyl)-3,6-dimethylquinoline, 14.0 g (0.05 mole) of iridium (III) chloride hydrate (Ir(III)Cl$_3$.3H$_2$O), 280 ml of 2-ethoxyethanol and 140 ml of distilled water (H$_2$O) were refluxed in a dry three-neck round-bottom flask for 24 hours. The reaction mixture was cooled to room temperature and water was added thereto to precipitate a crystal. The crystal was collected by filtration and washed with water to give 13.0 g of a dimeric complex. 13.0 g (0.01 mole) of the dimeric complex, 1.6 g (0.02 mole) of acetylacetone, 3.3 g (0.03 mole) of sodium carbonate (Na$_2$CO$_3$) and 260 ml of 2-ethoxyethanol were stirred in a dry three-neck round-bottom flask at room temperature for 24 hours. Thereafter, water was added to the reaction mixture to precipitate a crystal. The crystal was collected by filtration and washed with methanol, affording 5.0 g of the target product.

$^1$H NMR (300 MHz, CDCl$_3$): δ 8.23-8.33 (d, 2H), 8.08-8.18 (d, 2H), 7.85-7.95 (s, 2H), 7.42-7.52 (s, 2H), 7.12-7.18 (dd, 2H), 7.05-7.12 (d, 2H), 6.74-6.84 (s, 2H), 4.52-4.58 (s, 1H), 3.00-3.15 (s, 6H), 2.40-2.55 (s, 6H), 1.35-1.50 (s, 6H), 0.05-0.25 (s, 18H)

Comparative Example 2-(2)

Fabrication of Organic Electroluminescent Device

An organic electroluminescent device was fabricated in the same manner as in Example 1 except that the iridium complex compound prepared in Comparative Example 2-(1) was used instead of the iridium complex compound prepared in Example 1-(1).

Comparative Example 3

Comparative Example 3-(1)

Synthesis of Iridium Complex Compound

The above iridium complex compound was prepared to compare with the red phosphorescent compounds of the present invention.

In the structure of the comparative compound, methyl groups are substituted at the 6-positions of the quinoline rings.

The comparative iridium complex compound was prepared by the following procedure. First, 27.7 g (0.11 mole) of 2-(4-methylphenyl)-3,6-dimethylquinoline, 16.0 g (0.05 mole) of iridium (III) chloride hydrate (Ir(III)Cl$_3$.3H$_2$O), 320 ml of 2-ethoxyethanol and 160 ml of distilled water (H$_2$O) were refluxed in a dry three-neck round-bottom flask for 24 hours. Then, the reaction mixture was cooled to room temperature and water was added thereto to precipitate a crystal. The crystal was collected by filtration and washed with water to give 23.7 g of a dimeric complex. 23.7 g (0.02 mole) of the dimeric complex, 3.5 g (0.03 mole) of acetylacetone, 7.0 g (0.07 mole) of sodium carbonate (Na$_2$CO$_3$) and 474 ml of 2-ethoxyethanol were stirred in a dry three-neck round-bottom flask at room temperature for 24 hours. Thereafter, water was added to the reaction mixture to precipitate a crystal. The crystal was collected by filtration and washed with methanol, affording 5.0 g of the target product.

$^1$H NMR (300 MHz, CDCl$_3$): δ 8.12-8.22 (d, 2H), 7.98-8.08 (d, 2H), 7.80-7.90 (s, 2H), 7.40-7.50 (s, 2H), 7.08-7.18 (dd, 2H), 6.74-6.84 (dd. 2H), 6.45-6.58 (s, 2H), 4.35-4.45 (s, 1H), 3.00-3.15 (s, 6H), 2.40-2.55 (s, 6H), 1.90-2.05 (s, 6H), 1.30-1.45 (s, 6H)

Comparative Example 3-(2)

Fabrication of Organic Electroluminescent Device

An organic electroluminescent device was fabricated in the same manner as in Example 1 except that the iridium complex compound prepared in Comparative Example 3-(1) was used instead of the iridium complex compound prepared in Example 1-(1).

Comparative Example 4

Comparative Example 4-(1)

Synthesis of Iridium Complex Compound

The above iridium complex compound was prepared to compare with the red phosphorescent compounds of the present invention.

In the structure of the comparative compound, methyl groups are substituted at the 6-positions of the quinoline rings and the 3- and 5-positions of the phenyl rings. The comparative iridium complex compound was prepared by the following procedure. First, 40.0 g (0.16 mole) of 2-(3,5-dimethylphenyl)-6-methylquinoline, 23.0 g (0.08 mole) of iridium (III) chloride hydrate ($Ir(III)Cl_3 \cdot 3H_2O$), 690 ml of 2-ethoxyethanol and 230 ml of distilled water ($H_2O$) were refluxed in a dry three-neck round-bottom flask for 24 hours. Then, the reaction mixture was cooled to room temperature and water was added thereto to precipitate a crystal. The crystal was collected by filtration and washed with water to give 40.0 g of a dimeric complex. 40.0 g (0.03 mole) of the dimeric complex, 8.3 g (0.08 mole) of acetylacetone, 11.8 g (0.11 mole) of sodium carbonate ($Na_2CO_3$) and 1,200 ml of 2-ethoxyethanol were stirred in a dry three-neck round-bottom flask at room temperature for 24 hours. Thereafter, water was added to the reaction mixture to precipitate a crystal. The crystal was collected by filtration and washed with methanol, affording the target product.

$^1$H NMR (300 MHz, $CDCl_3$): δ 7.98-8.08 (s, 4H), 7.80-7.88 (d, 2H), 7.58-7.62 (s, 2H), 7.46-7.50 (s, 2H), 7.12-7.20 (dd, 2H), 6.47-6.55 (s. 2H), 4.30-4.45 (s, 1H), 2.41-2.47 (s, 6H), 2.34-2.40 (s, 6H), 1.33-1.39 (s, 6H), 1.22-1.29 (s, 6H)

Comparative Example 4-(2)

Fabrication of Organic Electroluminescent Device

An organic electroluminescent device was fabricated in the same manner as in Example 1 except that the iridium complex compound prepared in Comparative Example 4-(1) was used instead of the iridium complex compound prepared in Example 1-(1).

Test Example 1

The organic electroluminescent devices fabricated in Examples 1 to 5 and Comparative Examples 1 to 4 were tested for voltage, current, quantum efficiency, luminance, chromaticity coordinates and lifetime. The results are shown in Table 1.

TABLE 1

| | Voltage (V) | Current (mA) | Luminance (cd/m$^2$) | Quantum efficiency (Q.E) | Current efficiency (cd/A) | Power efficiency (lm/W) | CIE (X) | CIE (Y) | Lifetime, T80 (hr) |
|---|---|---|---|---|---|---|---|---|---|
| Ex. 1 | 5.5 | 0.9 | 1,421 | 20.6 | 14.2 | 8.2 | 0.675 | 0.324 | 202 |
| Ex. 2 | 5.4 | 0.9 | 1,111 | 19.4 | 11.1 | 6.5 | 0.685 | 0.314 | 140 |
| Ex. 3 | 5.3 | 0.9 | 1,375 | 20.8 | 13.8 | 8.1 | 0.667 | 0.331 | 65 |
| Ex. 4 | 5.2 | 0.9 | 1,867 | 21.0 | 18.7 | 11.3 | 0.662 | 0.337 | 76 |
| Ex. 5 | 5.3 | 0.9 | 1,630 | 23.5 | 16.3 | 9.7 | 0.676 | 0.323 | 132 |
| Comp. Ex. 1 | 5.5 | 0.9 | 1,445 | 13.7 | 14.5 | 8.2 | 0.635 | 0.360 | 29 |
| Comp. Ex. 2 | 5.5 | 0.9 | 882 | 12.9 | 8.8 | 5.1 | 0.662 | 0.332 | 89 |
| Comp. Ex. 3 | 5.2 | 0.9 | 1,153 | 14.4 | 11.5 | 6.9 | 0.649 | 0.348 | 63 |
| Comp. Ex. 4 | 5.4 | 0.9 | 1,034 | 11.7 | 10.3 | 6.0 | 0.662 | 0.337 | 29 |

As can be seen from the results in Table 1, the x values, which represent red color purity, on the CIE chromaticity coordinates of the organic electroluminescent devices fabricated in Examples 1 to 5 were comparable to or higher than those of the comparative organic electroluminescent devices fabricated in Comparative Examples 1 to 4.

As the red color purity of conventional organic electroluminescent devices increases (i.e. the x values on CIE chromaticity coordinates increase), the luminance and quantum yield of the devices decrease. In contrast, the quantum efficiency of the organic electroluminescent devices fabricated in Examples 1 to 5 was much higher than that of the organic electroluminescent devices fabricated in Comparative Examples 1 to 4 despite their higher x values on the CIE chromaticity coordinates. In addition, the organic electroluminescent devices fabricated in Examples 1 to 5 as a whole showed excellent characteristics in terms of power efficiency, luminance and lifetime over the organic electroluminescent devices fabricated in Comparative Examples 1 to 4.

What is claimed is:

1. A red phosphorescent compound of Formula 1:

(1)

wherein $R_1$, $R_2$, $R_3$, $R_4$, $R_5$ and $R_6$ are independently a hydrogen atom, a $C_1$-$C_{18}$ alkyl group, a $C_1$-$C_{18}$ alkoxy group, a halogen atom, a $C_1$-$C_{18}$ haloalkyl group, a substituted or unsubstituted $C_5$-$C_{18}$ aryl group, a $C_5$-$C_{18}$ cycloalkyl group, or a substituted or unsubstituted 5- to 18-membered aromatic heterocyclic group containing at least one heteroatom selected from N, O and S atoms, with the proviso that the substituted aryl group and the substituted aromatic heterocyclic group is substituted with at least one substituent selected from the group consisting of $C_1$-$C_{10}$ alkyl, $C_1$-$C_{10}$ alkoxy, cyano, $C_1$-$C_{10}$ alkylamino, alkylsilyl, halogen, $C_6$-$C_{10}$ aryl, $C_6$-$C_{10}$ aryloxy, $C_6$-$C_{10}$ arylamino, $C_6$-$C_{10}$ arylsilyl, and $C_3$-$C_{19}$ heteroaryl; each X is a trialkylsilyl group; and $A_1$, $A_2$ and $A_3$ are independently a hydrogen atom, a $C_1$-$C_{18}$ alkyl group, a halogen atom, a $C_1$-$C_{18}$ haloalkyl group, a $C_5$-$C_{18}$ aryl group or a $C_5$-$C_{18}$ cycloalkyl group, with the proviso that $A_2$ is optionally bonded to $A_1$ or $A_3$ to form a ring.

2. The compound according to claim 1, wherein the trialkylsilyl group is trimethylsilyl.

3. The compound according to claim 1, wherein the red phosphorescent compound is selected from the group consisting of the following compounds (2-1 to 2-20):

(2-1)

(2-2)

(2-3)

(2-4)

(2-5)

(2-6)

(2-7)

(2-8)

(2-9)

(2-10)

(2-11)

(2-12)

(2-13)

4. An organic electroluminescent device comprising an anode, an organic light-emitting layer and a cathode wherein the organic light-emitting layer contains the compound according to claim 1.

5. The device according to claim 4, further comprising a hole transport layer disposed between the anode and the organic light-emitting layer.

6. The device according to claim 5, further comprising a hole injecting layer disposed between the anode and the hole transport layer.

7. The device according to claim 4, further comprising an electron transport layer disposed between the organic light-emitting layer and the cathode.

8. The device according to claim 7, further comprising an electron injecting layer disposed between the cathode and the electron transport layer.

* * * * *